United States Patent [19]

Wurschum

[11] Patent Number: 5,242,659
[45] Date of Patent: Sep. 7, 1993

[54] DEVICE FOR FEEDING OBJECTS INTO A WASTE BIN OF AN ANALYZER

[75] Inventor: Hans P. Wurschum, Ostfildorn, Fed. Rep. of Germany

[73] Assignee: Eastman Kodak Company, Rochester, N.Y.

[21] Appl. No.: 913,556

[22] Filed: Jul. 14, 1992

[30] Foreign Application Priority Data

Jul. 16, 1991 [DE] Fed. Rep. of Germany ....... 4123533

[51] Int. Cl.$^5$ ............................................. G01N 21/13
[52] U.S. Cl. ........................................ 422/65; 422/63; 422/64; 422/67; 422/68.1
[58] Field of Search ........................ 422/63, 64, 65, 67, 422/68.1

[56] References Cited

U.S. PATENT DOCUMENTS

| 4,152,390 | 5/1979 | Nosco et al. | 422/63 |
| 4,287,155 | 9/1981 | Tersteeg et al. | 422/64 |
| 4,296,069 | 10/1981 | Smith et al. | 422/64 |
| 4,303,611 | 12/1981 | Jessop | 422/65 |
| 4,568,519 | 2/1986 | Hamilton et al. | 422/64 |
| 4,710,352 | 12/1987 | Slater et al. | 422/65 |
| 4,794,085 | 12/1988 | Jessop et al. | 436/54 |
| 4,946,650 | 8/1990 | Röthele | 422/68.1 |
| 5,008,082 | 4/1991 | Shaw | 422/63 |
| 5,053,198 | 10/1991 | Quenin | 422/64 |
| 5,080,864 | 1/1992 | Show et al. | 422/62 |
| 5,085,832 | 2/1992 | Show et al. | 422/63 |

Primary Examiner—James C. Housel
Assistant Examiner—Harold Y. Pyon
Attorney, Agent, or Firm—Dana M. Schmidt

[57] ABSTRACT

An analyzer having a chute for directing disposable tips to a waste bin in the analyzer. The chute is located at the intersection point created by the path of the aspirating mechanism and the path of the tray of containers used by the aspirating mechanism. The chute is movably mounted so as to be movable out of the way when a tray is presented at the intersection path.

12 Claims, 3 Drawing Sheets

DEVICE FOR FEEDING OBJECTS INTO A WASTE BIN OF AN ANALYZER

FIELD OF THE INVENTION

The invention relates to a device for feeding objects into a waste bin of an analyzer comprising a transport path, a transport carriage for a tray carrying a container and a processing station having an aspirating head for substances to be analyzed.

BACKGROUND OF THE INVENTION

Various analyzers are known disclosing devices for feeding objects into a waste bin. For example, an analyzer is shown in U.S. Pat. No. 4,287,155 in which a waste bin is arranged in the area of a processing station beneath an aspirating head and adjacent to trays carrying pipette tips or containers filled with liquids to be analyzed. In this device, the aspirating head picks up a pipette and after use, i.e., after aspiration and distributing the liquid to be analyzed, strips the top and drops it into the waste bin.

Such constructions have worked satisfactorily in the past. Difficulties arise, however, when attempts are made to design an analyzer to be more compact—a need that arises for analyzers with scaled-down volumes. The waste bin ends up getting in the way of other components, e.g., in the way of the path of trays that feed to the aspirating head. If the stripping step and disposal bin are moved over out of the way of the trays, as in the prior art, then that moved-over location is one more station for which room has to be made in the analyzer—the very problem sought to be eliminated.

Therefore, there has been a need, prior to this invention, to find a way to overlap the waste bin of the aspirating head, and a tray path, so that space can be minimized in the analyzer, particularly those designed for reduced throughput and smaller space.

SUMMARY OF THE INVENTION

The above need has been met by a clinical analyzer comprising a transport carriage constructed to carry a tray of containers, means for mounting the carriage on a first transport path, a processing station comprising aspirating means for aspirating and dispensing substances to be analyzed using disposable tips, means for moving the aspirating means on a second path that intersects the first path at an aspirating and dispensing station, and disposing means at the station for disposing of waste articles used in the aspirating and dispensing. The device is improved in that it further includes a feeding chute for directing waste articles to a waste bin, mounting means for movably mounting the chute at the station so that it is movable from a first position in communication with the aspirating means but blocking the first path, to a second position unblocking the first path but out of communication with the aspirating means, so that the chute can occupy space otherwise occupied by other parts of the analyzer when the chute is not needed.

Accordingly, it is an advantageous feature of the invention that a waste chute for tips can be located at the same place as the path of trays for liquid, saving space, without interfering with the operation of the tray.

It is a further advantageous feature of the invention that the processing station is shut down when the feeding chute has been removed and, thus, a used pipette cannot be thrown off from the aspirating head.

Further features and advantages can be inferred from the following description of the embodiments of the invention and the drawings.

IN THE DRAWINGS

Figure 1:
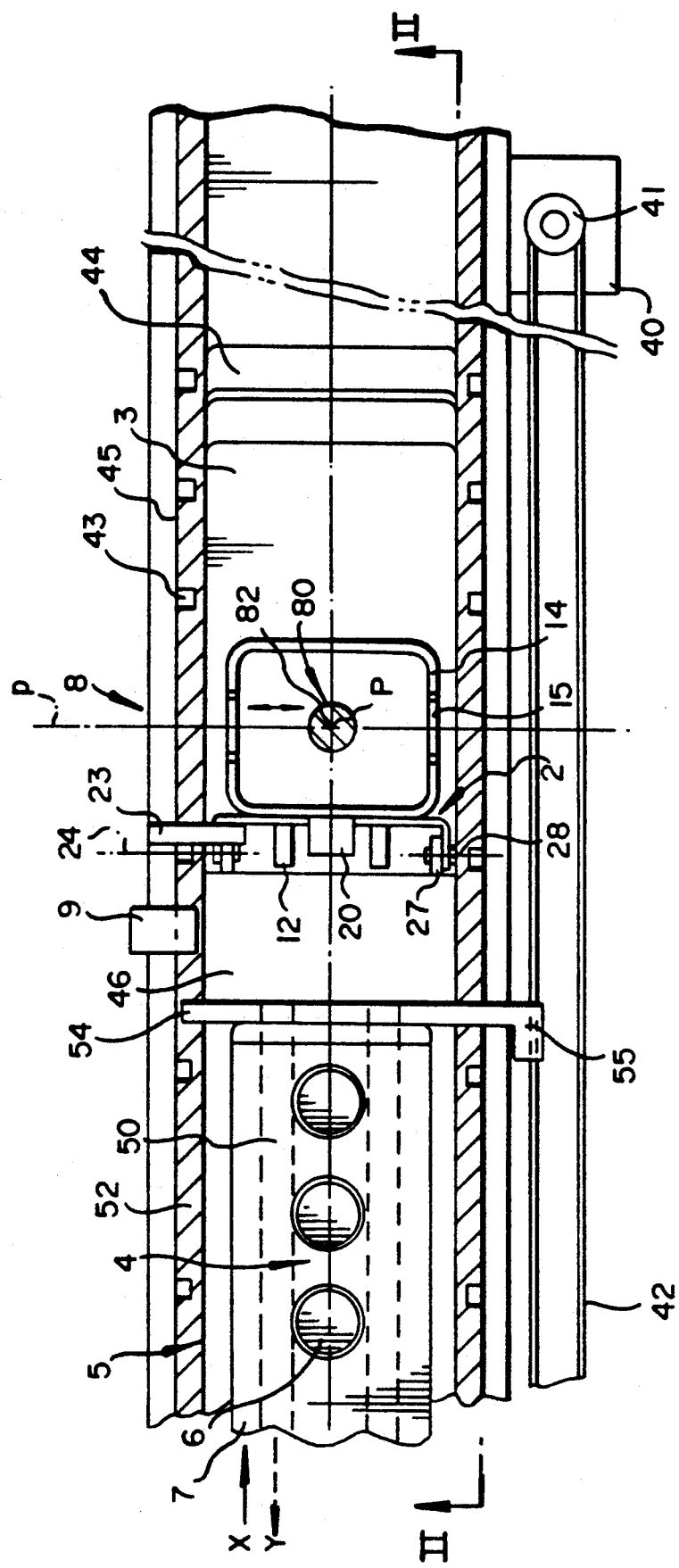
FIG. 1 shows a top view of the device according to the invention and a section of the transport path.

The invention is particularly described in connection with trays used for diluting sample obtained from elsewhere in the analyzer, the diluted sample then being deposited onto a dry slide element such as the "Ektachem" TM slide elements obtainable from Eastman Kodak Co. In addition, however, the liquid of the containers in the trays can be any liquid, even sample liquid, and the eventual dispensing for analysis can be into reaction cuvettes for a wet assay carried on elsewhere in the incubator.

Clinical analyzers using this invention conventionally include a source of sample, a source of reagents (either wet or dried in slide format), an incubator, and a read station. Since these are conventional, they are not shown in the drawings.

The disposal or feeding chute 1 of the invention is used primarily to dispose of the disposable tips used for dilution, but can be used also for disposal of any disposables that have access to the chute.

In accordance with the invention the device illustrated in FIG. 1 cocomprises a feeding chute 1 and a chute-mounting means 2 which are arranged within a recess 44 in a transport path 4 and above a waste bin 3. Means 2 having a blocking finger 20 is supported by two bearings 28 via pins 28 and starting from a stop member 23 can be pivoted about a fulcrum 24 along the longitudinal axis of the transport path. Finger 20 acts as a sensing means to signal to the device when chute 1 has been removed.

Feeding chute 1 is illustrated in its feed position 10 in which in the area of a processing station 8 its vertically extending center axis is oriented towards an aspirating station 82 located below an aspirating head 80 for liquids to be aspirated so that a pipette tip 81 can be stripped off (see FIG. 2). Conventional means are provided, not shown, to move head 80 along path "p", FIG. 1.

Override means are arranged on feeding chute 1 connecting it to the means 2 for overriding the signalling effect of finger 20. The chute comprises a hollow cylinder made of a chemically resistent plastic material and having a square cross-section. The override means is comprise preferably a flange 12 which projects out beyond the reach of finger 20 when the chute is returned to means 2.

A transport carriage 5 having a tray 7 which carries a container 6 is arranged on transport path 4 and supported by a surface 46 of transport path 4 via its two skids 50. Carriage 5 is provided with lateral ribs 52 cooperating with guides 45 and hold-down means 43 of the transport path. The skids are the primary means for pushing chute 1 out of its vertical position.

The skids 50 have a distance from each other which corresponds to the distance of means 12 at the feeding chute. At a front wall facing the feeding chute 1 transport carriage 5 is provided with a flag 54 cooperating with a sensor 9 arranged at the transport path 4 and a tray movement member 55 on the opposite side.

Tray movement member 55 is connected to an endless drive belt 42 which runs outside and along transport path 4 and is guided around a drive pulley 41 of a microprocessor-controlled stepper motor 40 and an idling pulley (not illustrated).

Figure 2:
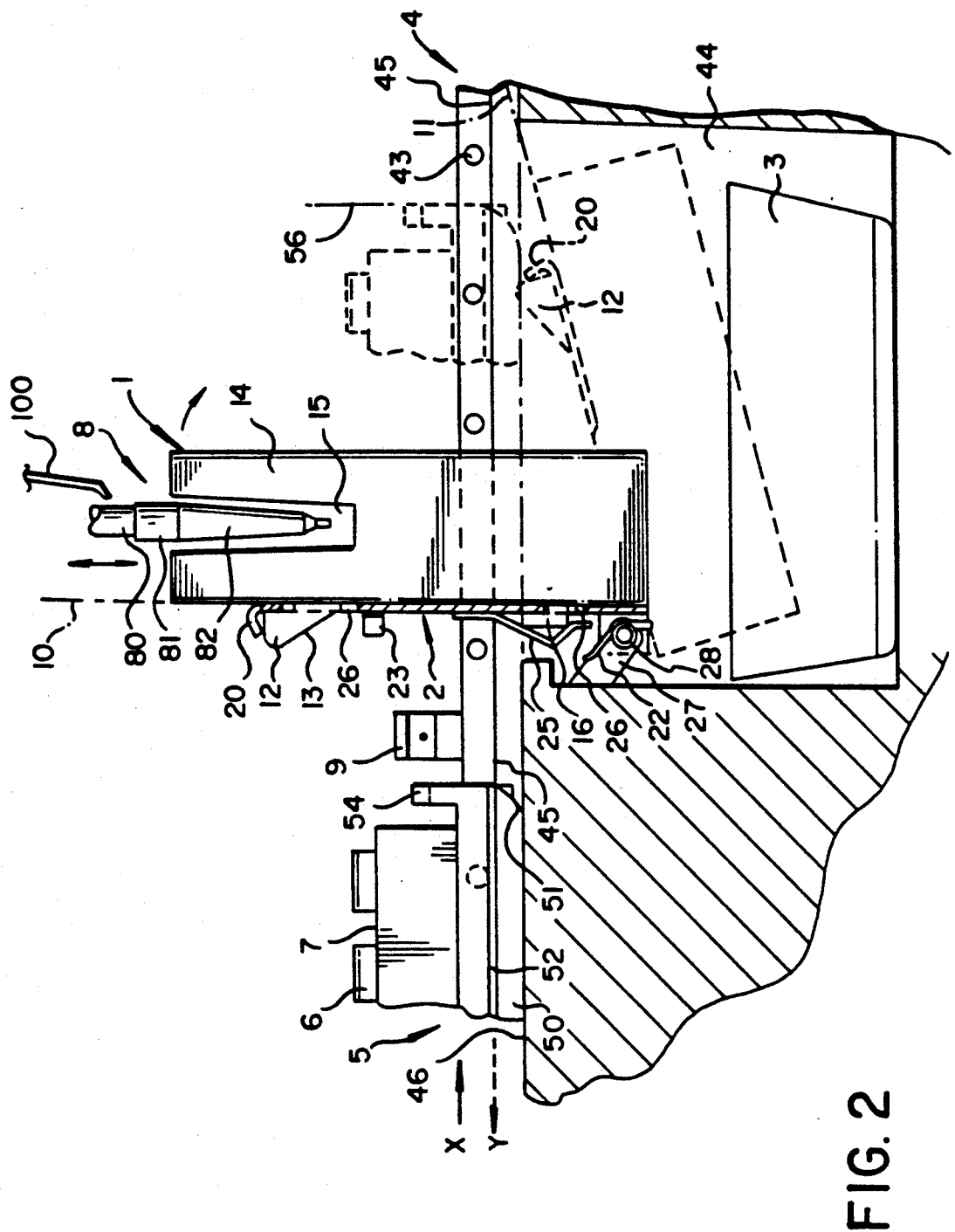
FIG. 2 shows a lateral view of the device according to FIG. 1 in cross-section along a long A—A of FIG. 1.

In FIG. 2, the feeding chute 1 is shown in its vertical feed position for throwing a pipette 81 into a waste bin 3 in its horizontal end position 11 (in phantom) for removing liquids from the containers 6 by means of the aspirating head 80.

On bearings 27, the feeding chute 1 is provided with resetting means 22 shaped as leg springs urging the chute against stop member 23 into the feed position 10.

The side walls 14 of chute 1 extend high enough to give splash protection to trays 7 when tips 81 are dropped into the chute.

In two of its side walls 14 extending along transport path 4 the feeding chute 1 has recesses 15 located at the level of the aspirating head 80 and forming a passage for the aspirating head with a pipette 81 inserted therein. Furthermore, in the area above bearing 27 the feeding chute 1 has an additional holding element 16 projecting through an aperture 26 on mounting means 2 and is centered and fixed to the retainer by a leaf spring 25. Flange 12 of feeding chute 1 is provided with a camming ramp (13) having a height which is greater than that of the finger 20 so that when feeding chute 1 has been pivoted into its end position 11 the flange 12 formed on means 2 define part of the sliding surface 46 for the skids 50 of transport carriage 5. Chamfers 51 are provided on the front edges of skids 50. Flange 12 thus acts to guide tray 5 over finger 20, as shown in phantom, thus disabling the function of that finger.

Figure 3:
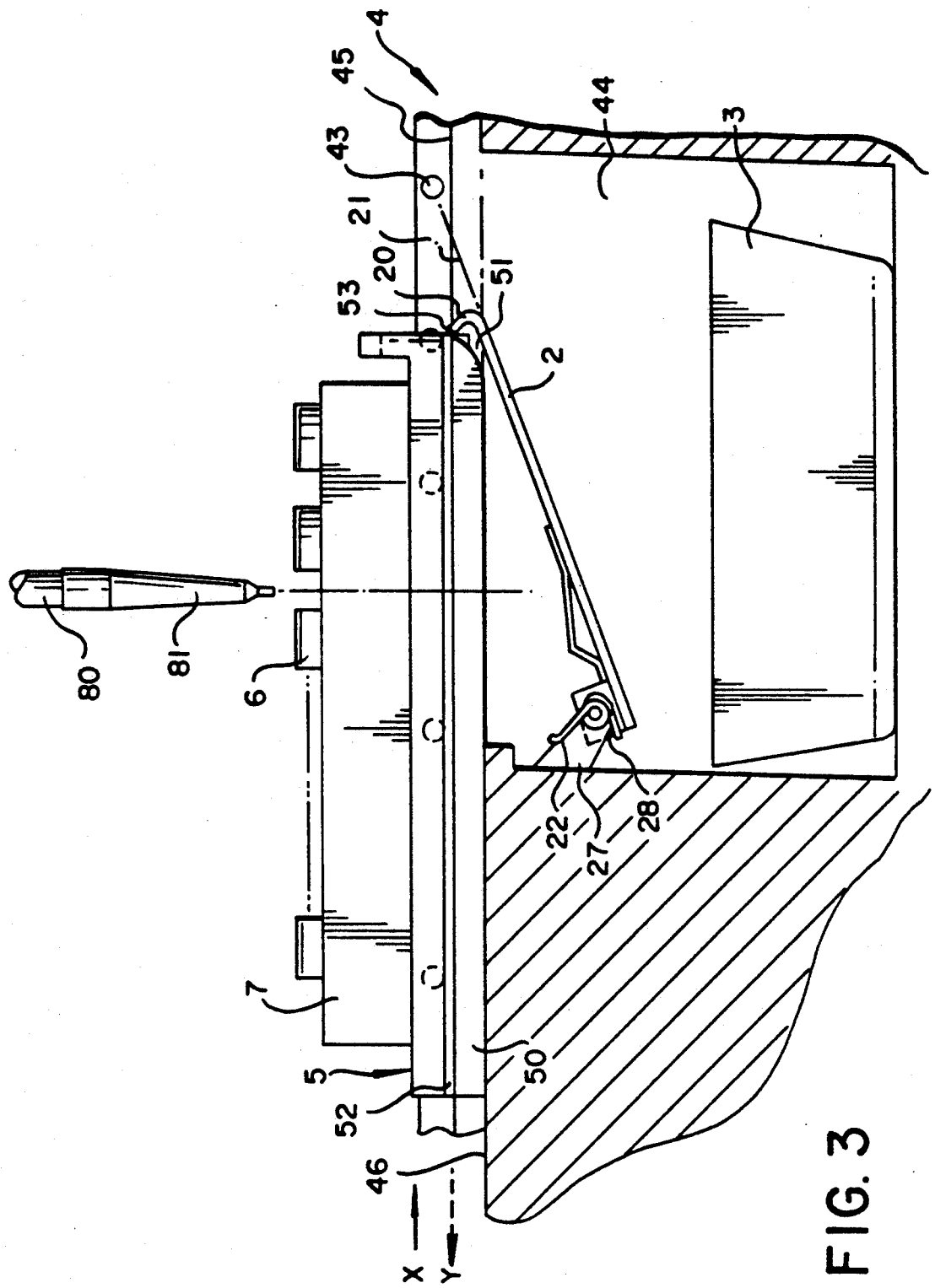
FIG. 3 is the device according to FIG. 2 in a further functional representation.

FIG. 3 shows mounting means 2 in its end position 21 with the feeding chute 1 being removed. The leading edge 53 of transport carriage 5 contacts finger 20 extending into the transport path 4 and carriage 5 is thus in a position in which the aspirating head 80 is oriented halfway between two adjacent containers 6 held in tray 7. Alternatively (not shown), automated motor means separate and apart from carriage 5 can be used to pivot chute 1 out of the way as a carriage approaches, so that skids 50 would not have to perform this function.

The device operates as follows: Path 4 and path "p" intersect at point "P", FIG. 1, to allow discharge or collection of liquid in containers 6 from tip 81. Initially, a tray 7 carrying containers 6 holding liquids to be analyzed is placed on transport carriage 5 in an input station not illustrated. After starting a microprocessor-controlled program for making a sample analysis the transport carriage 5 is moved by means of stepper motor 40 on transport path 4 in the first direction (X) to reach the feeding chute 1 positioned in its feeding position. Before transport carriage 5 reaches the feeding chute 1 flag 54 passes an optoelectrical sensor 9 producing a signal for counting the steps of the stepper motor 40 by means of a microprocessor-controlled control unit (not illustrated)—see FIG. 1. Then transport carriage 5 knocks against mounting means 2 of feeding chute 1 and pivots it along the transport path 4 into recess 44. During further movement, the transport carriage 5 slides with its skids 50 over flange 12 of mounting means 2 until it reaches an end position 56 corresponding to a rated value, i.e. a predetermined number of steps. By means of its guide ribs 52 the transport carriage 5 is held between the guides 45 and the hold-down means 43 of the transport path 4 (see FIG. 2). Subsequently, the direction of rotation of stepper motor 40 is reversed and transport carriage 5 returned in the second direction (Y) until flag 54 again reaches sensor 9. If the number of steps in the second direction (Y), which corresponds to the actual value, is identical with the rated value, the control unit detects that a feeding chute 1 is attached to mounting means 2.

This allows the transport carriage 5 to be moved again in the first direction (X) until the central axis of the foremost container 6 is located beneath the aspirating station 82 of the aspirating head 80 equipped with a pipette tip 81.

After removal of the liquid from container 6 and during mixing with a sample liquid to be analyzed in a further processing station (not illustrated), the transport carriage 5 is moved in the second direction (Y) until the feeding chute 1 has been pivoted back to its feed position 10 by means of the resetting means 22. When the mixing and distributing procedure of the liquid is finished, the aspirating head 80 is returned to the aspirating station 82 by guiding it normal to the transport path 4 into the feeding chute 1 through recess 15 in side wall 14. Subsequently, the used-up pipette 81 is stripped from the aspirating head 80 by, e.g., a stripping finger 100, FIG. 2, and thrown into waste bin 3 which for emptying can be removed from recess 44 of transport path 4. Aspirating head 80 is then moved out of aspirating station 82 to receive a new pipette tip 81. This procedure is repeated until all liquids to be analyzed of containers 6 are used up.

When inserting a new tray 7 with the feeding chute being removed from mounting means 2 and, by mistake, not having been re-attached, the leading edge 53 of transport carriage 5 will abut finger 20 of mounting means 2 and be stopped during subsequent movement of the carriage in the first direction (X) (see FIG. 3). Stepper motor 40, however, which is slowed down continues to receive its predetermined number of control pulses by the control unit.

During the subsequent return movement in the second direction (Y) a smaller stepping number for the stepper motor 40 will thereby result, which corresponds to a smaller actual value.

This actual value is detected by the control unit as a feeding chute 1 removed from means 2 and indicated to the user by a display means not illustrated. Moreover, the control unit effects a shut-down of processing station 8. Dumping a used-up pipette 81 is however prevented in order to avoid contamination of the liquids of containers 6 and the analyzer itself.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In a clinical analyzer comprising a transport carriage constructed to carry a tray of containers, means for mounting and moving said carriage on a first transport path, a processing station comprising aspirating means for aspirating and dispensing substances to be analyzed using disposable tips, means for moving said aspirating means on a second path that intersects said first path at an aspirating and dispensing station, and disposing means at said processing station for disposing of tips used in said aspirating and dispensing;

the improvement wherein said disposing means comprises a feeding chute at said aspirating and dispensing station for direction tips to a waste bin in the analyzer, mounting means for pivotally mounting said chute at said aspirating and dispensing station so that it is pivotable from a first position in communication with said aspirating means but blocking said first path, to a second position unblocking said first path but out of communication with said aspirating means.

2. An analyzer as defined in claim 1, wherein said chute and said carriage include cooperating surfaces that allow said carriage to push said chute to said second position when said chute is present in the analyzer.

3. An analyzer as defined in claims 1 or 2 wherein said chute is pivotally mounted at said station to pivot between said two positions.

4. An analyzer as defined in claims 1 or 2 wherein said aspirating and dispensing means include means for stripping therefrom a disposable tip ready for the waste bin, and wherein said chute includes side walls sufficient in their extension to protect said tray and containers therein from splashing by tips stripped from said aspirating means when they fall within said chute, and wherein said mounting means includes means for removably mounting said chute thereon to allow removal and cleaning of said side walls.

5. An analyzer as defined in claim 4, and further including sensing means for signalling the removal of the chute from said mounting means, said sensing means including a sensing finger on said mounting means.

6. An analyzer as defined in claim 5, and further including disabling means on said chute for disabling said sensing means when said chute is assembled on said mounting means.

7. An analyzer as defined in claim 6, wherein said override means comprise a tray-lifting flange that projects beyond said finger when said chute is assembled.

8. An analyzer as defined in claim 6, wherein said disabling means comprise a skid surface on the bottom of said carriage curved to cooperate with said flange t lift the tray over said finger.

9. An analyzer as defined in claims 1 or 2, and further including means for biasing said chute in said blocking position.

10. An analyzer as defined in claims 1 or 2, and further including a sensor along said first path for sensing the presence of one of said carriages.

11. An analyzer as defined in claim 10, and further including means for preventing stripping of tips from said aspirating means if said chute is mixing from said mounting means.

12. In a clinical analyzer comprising an aspirating means for collecting or delivering liquid to a container, said aspirating means using disposable tips. means for moving said aspirating means along a first path, trays of containers, means for moving said trays along a second path, said paths crossing within said analyzer at an intersection point where liquid is delivered or collected in said trays by or from said aspirating means, and a waste bin for collecting a disposable tip from said aspirating means, the improvement wherein said waste bin is disposed under said intersection point to save space, and further including a guide chute located between said bin and said aspirating means at said intersection point, said chute being movably mounted so as to be moved out of the second path by a tray presented at said intersection point.

* * * * *

UNITED STATES PATENT AND TRADEMARK OFFICE
CERTIFICATE OF CORRECTION

PATENT NO.   :   5,242,659
DATED        :   September 7, 1993
INVENTOR(S)  :   Hans P. Wurschum It is certified that error appears in the above-identified patent and that said Letters Patent is hereby corrected as shown below:

Column 5, line 7 should read --pensing station for directing tips to a waste bin in--.

Column 6, line 19 should read --said aspirating means if said chute is missing from said--.

Signed and Sealed this

Twenty-sixth Day of April, 1994

Attest:

BRUCE LEHMAN

Attesting Officer     Commissioner of Patents and Trademarks